US006551339B2

(12) United States Patent
Gavronsky

(10) Patent No.: US 6,551,339 B2
(45) Date of Patent: Apr. 22, 2003

(54) ACUPUNCTURE DEVICE WITH IMPROVED NEEDLE GUIDE TUBE

(76) Inventor: Stas Gavronsky, 39 Wayland Hills Rd., Wayland, MA (US) 01778

( * ) Notice: Subject to any disclaimer, the term of this patent is extended or adjusted under 35 U.S.C. 154(b) by 25 days.

(21) Appl. No.: 09/935,323

(22) Filed: Aug. 23, 2001

(65) Prior Publication Data

US 2003/0040767 A1 Feb. 27, 2003

(51) Int. Cl.[7] ................................................ A61B 17/34

(52) U.S. Cl. ...................................................... 606/189

(58) Field of Search ................................ 606/181, 184, 606/185, 186, 189, 172

(56) References Cited

U.S. PATENT DOCUMENTS 3,905,375 A * 9/1975 Toyama ...................... 606/189
3,939,841 A * 2/1976 Dohring et al. ............. 606/129
4,479,496 A * 10/1984 Hsu ........................... 606/189
4,950,279 A * 8/1990 Chang ........................ 606/189
5,624,460 A * 4/1997 Yoo ........................... 606/189
5,741,291 A * 4/1998 Yoo ........................... 606/189
5,792,171 A * 8/1998 Burdenko et al. .......... 606/189
5,904,700 A * 5/1999 Guo ........................... 606/189
6,022,368 A * 2/2000 Gavronsky et al. ......... 606/189
6,231,584 B1 * 5/2001 Gavronsky .................. 606/189

* cited by examiner

*Primary Examiner*—David O. Reip
*Assistant Examiner*—Victor Nguyen

(57) ABSTRACT

An acupuncture device consists of an acupuncture needle and a guide tube having a transverse, preferably V-shaped, slot through the tube wall. This slot is formed in the upper part of the guide tube and is substantially perpendicular to the axis of the tube. The handle of the needle is firmly secured inside the guide tube by a small elongated stopper made of an elastic material such as plastic or thick paper which is inserted into the V-shaped slot of the guide tube and squeezes the needle handle between its end and the inner wall of the tube opposite to the V-shaped slot. As the elastic stopper fits tightly into the V-shaped slot, it supports itself in the needle-securing position. Although the friction that the stopper creates through its pressure against the handle is sufficient to secure the needle inside the tube prior to the insertion, this friction yields to the downward motion of the needle during insertion so that the stopper does not present an obstacle for the insertion of the needle. After insertion of the needle, a practitioner pulls the stopper out and removes the guide tube in a conventional manner.

25 Claims, 2 Drawing Sheets

ACUPUNCTURE DEVICE WITH IMPROVED NEEDLE GUIDE TUBE

FIELD OF THE INVENTION

The present invention relates to the field of needle therapy, in particular to an acupuncture device with an improved needle guide tube.

BACKGROUND OF THE INVENTION

Acupuncture guide tubes are widely used in the practice of acupuncture to minimize discomfort during needle insertion. The guide tube allows quick insertion of an acupuncture needle through the epidermis. An example of a guide tube is the one shown in U.S. Pat. No. 5,792,171 issued in 1998 to Burdenko, et al. Fast puncturing of the patient's skin is important for pain-free insertion. There is typically 3–5 mm clearance between the upper end of the guide tube and the top of the handle of an acupuncture needle, which protrudes above the tube. The practitioner taps on the handle of the needle downward with his/her index finger while supporting the tube with the other hand. The needle, which has been resting on the surface of the patient's skin prior to insertion, is now inserted 3–5 mm through the skin into the acupuncture point. The guide tube has a diameter, which is bigger than the diameter of the handle of the acupuncture needle. This allows the removal of the guide tube after the insertion. On one hand, the relatively big diameter of the tube, in comparison with the shaft of the needle, provides more comfort for the patient by creating mild pressure around the acupuncture point and by providing firmness to the skin around that point. This feature is important for fast, pain-free insertion. On the other hand, the relatively big diameter of the tube compromises the precision of the insertion. This is because the tip of the needle is rarely in the center of the bottom opening of the tube prior to insertion, but at the sides, leaning against the inside tubular wall. The needle then tends to take diagonal orientation in respect to the tubular longitudinal axis. The tip of the needle, which rests on the skin, is at the bottom tubular wall opposite to the handle.

The practitioner is often unaware about an exact position of the needle. Hence, the angle at which the needle is inserted into the point is unpredictable. Furthermore, when the practitioner attempts to insert a needle at sharp angles, such as on the face or head of the patient, the acupuncture needle tends to slide downward, out of the guide tube. When the needle is inserted at a sharp angle to the surface of the skin, a very little clearance is left between the upper portion of the tube and the handle of the needle. This makes the regular insertion technique very uncomfortable, if not impossible. Also, the clearance is too small for full penetration of the tip of the needle through the epidermis. As a result, the patient may feel more pain than is necessary.

There are two reasons that contribute to the reduction of this clearance on top. One reason has to do with the thickness of the tubular wall. The acupuncture needle has to go a little forward and downward, over the small threshold formed by the bottom edge of the guide tube, to touch the skin. The other reason has to do with the fact that in the inclined position (angular insertion), both the tip of the needle and the handle of the needle are now against the same tubular wall. This contributes to the additional "slip out" of the needle at the skin. It would be better, if the handle of the needle stayed at the opposite wall (diagonally), thus shortening the distance that the needle has to travel to reach the skin. But it is often hard to maintain this position of the handle during angular insertions because of the pressing of the handle of the needle against upper wall with index finger: there is not enough space between the handle and the skin. Sometimes, acupuncture insertions have to be performed against gravity. Needling of the points at the cervical spine with the patient in a sitting position is just one example of this. The acupuncture needle tends to slide out of the guide tube during such insertions, and regular insertion technique becomes impossible.

An attempt to solve the problem of the prior art was made in an acupuncture device with an improved guide tube described in U.S. Pat. No. 6,231,584 issued on May 15, 2001 to the same applicant. This acupuncture device consists of an acupuncture needle and a guide tube having a longitudinal slot or notch at the upper end of the tube, which is wider than the diameter of the needle handle. A practitioner can easily secure the upper portion of the handle in this notch by pressing on the handle of the needle with an index finger. In the case of angular insertions, the practitioner can maintain a desirable diagonal position of the needle inside the guide tube. The acupuncture operation is facilitated by making a larger portion of the needle handle projecting from the guide tube through the notch. According to another embodiment, the device is provided with a sleeve of a C-shaped configuration, which is fit onto the upper end of the guide tube. When the open part of the C-shaped configuration does not coincide with the aforementioned notch, and the handle of the needle stays inside the guiding tube, the whole device can be used in a conventional fashion. When the open part of the C-shaped configuration coincides with the aforementioned notch, the needle handle can be pushed through the notch, and when the sleeve is turned so that the groove is overlapped, the needle handle will be deflected and fixed between the lower edge of the sleeve and the bottom of the notch.

In spite of advantages, such as oblique insertion and insertion against gravity, the acupuncture device of U.S. Pat. No. 6,231,584 possesses some drawbacks. First, a provision of the C-shaped sleeve makes construction of the device more complicated. Second, C-sleeve requires tedious manipulations. Third, the acupuncture needle stays loose inside the guide tube during storage, and should be secured inside the guide tube by additional manipulation after removal from the package. Fourth, the needle has a diagonal position inside the guide tube, which some acupuncturists find inconvenient.

OBJECTS OF THE INVENTION

It is an object of the present invention to provide an acupuncture device with an improved needle guide tube which is free of the C-shaped sleeve, simple in construction, simple and convenient in manipulation, has a needle which is firmly secured inside the guide tube during storage and remains secured in the tube without additional manipulations after removal from the package, and is pressed against the inner wall of the tube and parallel to the longitudinal axis of the guide tube. A further object is to provide an acupuncture device with a needle stopper which secures the needle inside the guide tube and can be easily removed after completion of the acupuncture procedure. Another object is to provide a method of securing an acupuncture needle inside the guide tube for reliable fixation of the needle inside the guide tube during storage and after unpacking prior to use.

SUMMARY OF THE INVENTION

An acupuncture device of the invention consists of an acupuncture needle and a guide tube having a transverse, preferably V-shaped, slot through the tube wall. This slot is formed in the upper part of the guide tube and is substantially perpendicular to the axis of the tube. The handle of the needle is firmly secured inside the guide tube by a small elongated stopper made of an elastic material such as plastic or thick paper which is inserted into the V-shaped slot of the guide tube and squeezes the needle handle between its end and the inner wall of the tube opposite to the V-shaped slot. As the elastic stopper fits tightly into the V-shaped slot, it supports itself in the needle-securing position. Although the friction that the stopper creates through its pressure against the handle is sufficient to secure the needle inside the tube prior to the insertion, this friction yields to the downward motion of the needle during insertion so that the stopper does not present an obstacle for the insertion of the needle. The outer end of the stopper, which remains outside the guide tube after insertion of the stopper, is bent so that, after insertion of the stopper into the tube, it either remains in contact with the outer wall of the guide tube or is slightly bent outward from the outer wall of the tube at a small angle. After insertion of the needle, a practitioner pulls the stopper out and removes the guide tube in a conventional manner.

DETAILED DESCRIPTION OF THE INVENTION

Figure 2:
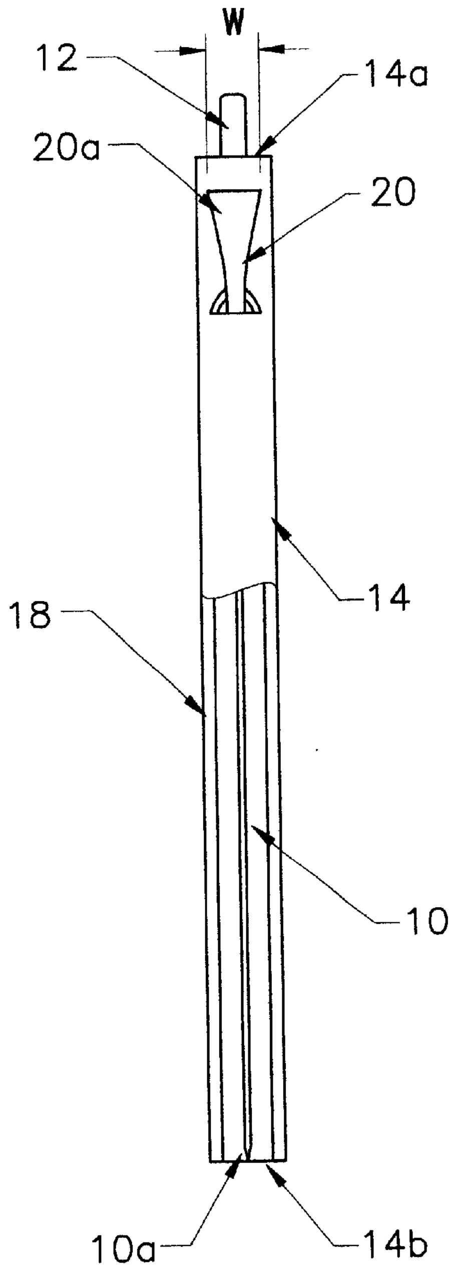
FIG. 2 is a view of the acupuncture device in the direction of arrow A of FIG. 1.
Figure 1:
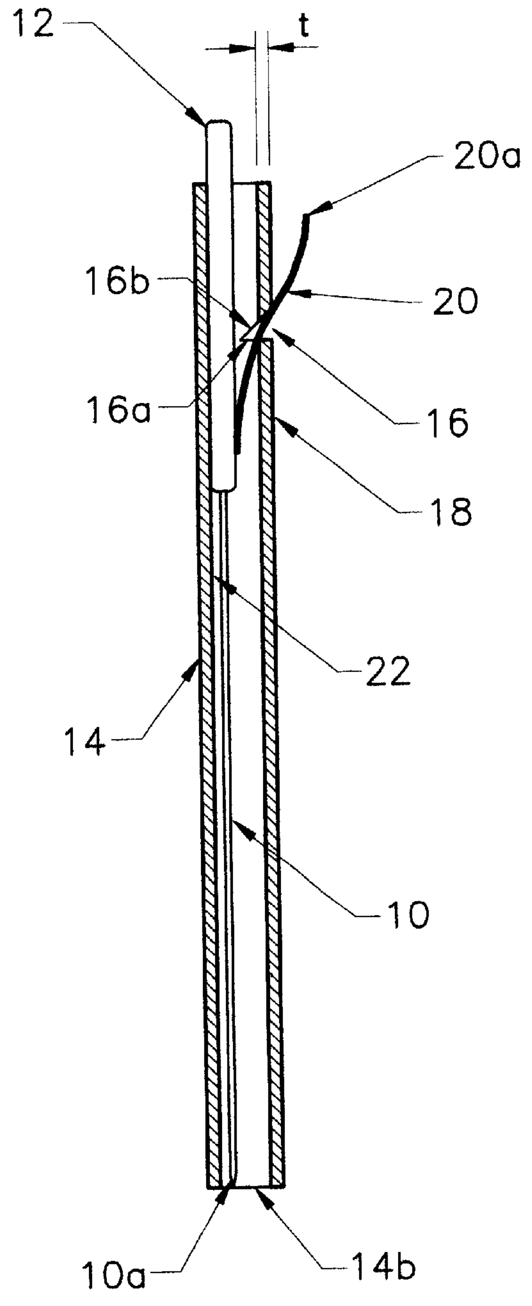
FIG. 1 is a longitudinal sectional view of an acupuncture device with a needle-securing stopper inserted into the transverse slot.

An acupuncture device of the invention with improved guide tube is shown in the attached drawings, where FIG. 1 is a longitudinal sectional view of the device with a needle-securing stopper inserted into the V-shaped slot, and FIG. 2 is a view of the acupuncture device in the direction of arrow A of FIG. 1.

It can be seen that the acupuncture device of the invention (which hereinafter will be referred to simply as a device) consists of an acupuncture needle 10 with a handle 12 and a guide tube 14 having a transverse slot 16 cut through the tube wall 18 (FIG. 1). The tube 14 may have any closed cross section such as circular, oval, ellipsoidal, or the line. The tube 14 has an open proximal end **14*a* and an open distal end 14*b***.

In a preferred embodiment, the slot 16 has a V-shaped configuration in a side view perpendicular to the direction of insertion of said stopper member see FIG. 1). shown in a side view of FIG. 1. The slot is cut in the direction transverse to the longitudinal axis X—X of the tube 14 and is formed by two planes: a first plane is substantially perpendicular to the longitudinal axis X—X of the tube and a seconds plane intersects the first one at an acute angle. The slot is formed in the third upper part of the guide tube 14 and is substantially perpendicular to the longitudinal axis of the tube 14.

The handle 12 of the needle 10 is firmly secured inside the guide tube by a small elongated stopper 20 made of an elastic material, such as plastic, rubber, small thin wooden strip, or thick paper, which is inserted into the V-shaped slot 16 of the guide tube 14 and squeezes the needle handle 12 between its end and the inner wall 22 of the tube 14 opposite to the V-shaped slot 16. The aforementioned V-shaped configuration of the slot 16 with a first cut plane **16*a* perpendicular to the axis and the second cut planel 16 barranged at an acute angle facilitates guiding of the end of the stopper 2 inserted into the tube 14 in an angular downward direction towards the needle handle 12. As the stopper 20 fits tightly into the V-shaped slot 16, it supports itself in the needle-securing position shown in FIG. 1**. Although paper and wood per se are not elastic materials, in the context of the present application they can be considered as elastic since a thin strip made of these materials will possess some resiliency in the direction transverse to the longitudinal direction of the plate.

Regarding the depth of the transverse slot 16, it may have a depth in the direction perpendicular to the longitudinal axis X—X within the range from the thickness "t" of the tube wall 18 (FIG. 1) to about half of the diameter of the tube 14. If the depth of the slot is less than the thickness "t" , the opening in the wall will be too small and it would be impossible to insert the stopper 20. if, on the other hand, the depth of the slot exceed half of the tube diameter, the cross section of the tube 14 in the area of the slot will be weakened and the tube can be easily broken during handling.

Although the friction that the stopper 20 creates through its pressure against the handle 12 is sufficient to secure the needle 10 inside the tube 14 prior to the insertion, this friction yields to the downward motion of the needle during insertion of the needle 10 into the patient's skin (not shown) so that the stopper 20 does not present an obstacle for insertion of the needle 10. The outer end **20*a* of the stopper 20, which remains outside the guide tube 14 after insertion of the stopper 20 into the V-shaped slot 16, is bent so that, after insertion of the stopper into the tube 14, it either remains in contact with the outer wall of the guide tube 14** or is slightly bent outward from the outer wall of the tube at a small angle.

As shown in FIG. 2, in order to protect the stopper 20 from falling into the guide tube 14, its outer end **20*a* may have a tapering shape with the largest width W greater than the width of the slot which may have the maximal size equal to the diameter of the tube 14 minus 2**t.

Figure 3:
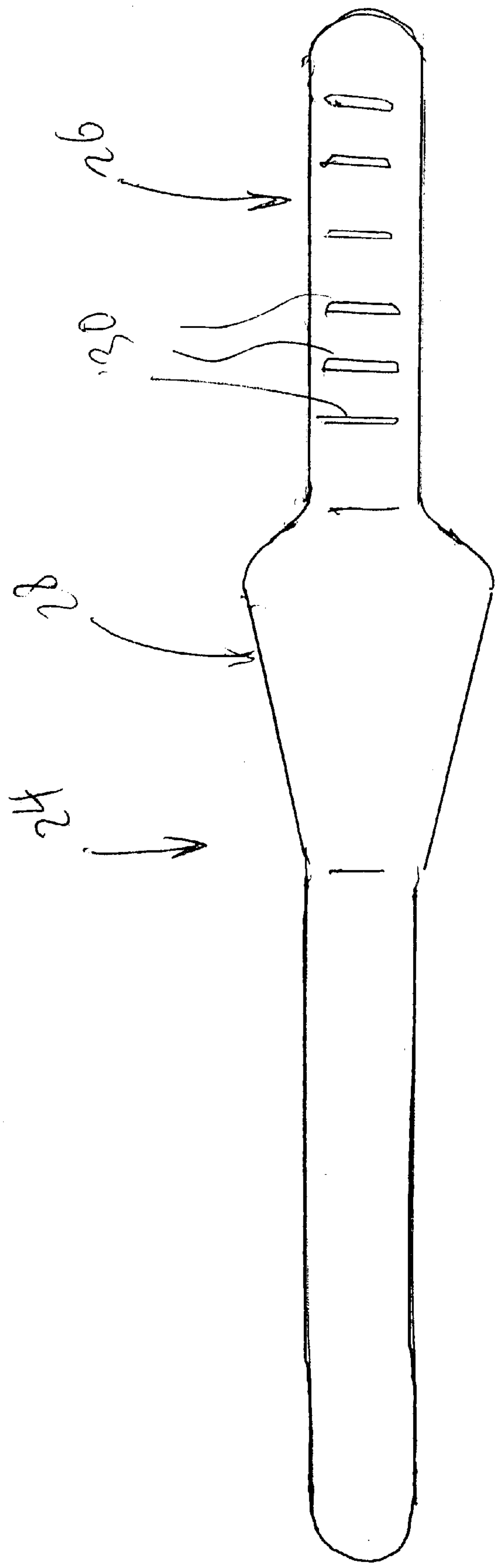
FIG. 3 is a plan view of a needle stopper in accordance with another embodiment of the invention.

FIG. 3 is a plan view of a needle stopper 24 made in accordance with another embodiment of the invention. In order to facilitate removal of the stopper 24, its tail portion 26 that protrudes outside the guide tube is made narrower than the broadened portion 28 and is provided with serrations 30 that increase the friction in gripping the tail portion 26 for removal of the stopper 24 from the guide tube.

In use, the acupuncturists unpacks the acupuncture device of the invention, which is stored pre-assembled with the guide tube 14, needle 10 with the handle 12, and the stopper 20, so that the needle handle 12 is secured inside the guide tube 14 by means of the resilient stopper 20. Prior to use, the tip **10*a* of the needle 10 does not project beyond the limits of the open distal end 14*b* of the guide tube 14. The end of the needle handle 12, however, projects from the open proximal end 14*a* of the tube 14 opposite to the needle tip by the amount sufficient for the insertion of the needle tip into the skin when the acupuncturists pushes on the handle 12. The acupuncturists is then inserts the tip 10*a* of the needle 10 into the patient's skin in a conventional manner by pushing on the projecting end of the needle handle 12 until the projecting end of the handle 12 fits completely in flush with the open proximal end 14*a*of the guide tube. After the needle 10 is inserted into the patient's skin, the acupuncturists pulls the stopper 20 out from the guide tube 14 through the transverse slot 16 and then gently removes the guide tube 14 from the needle 10 by sliding it upward along the needle 10 and its handle 12. Provision of serrations of projections 30 on the tail portion 26 of the stopper in the embodiment of FIG. 3** facilitates removal of the stopper from the guide tube.

Thus it has been shown that the invention provides an acupuncture device with an improved needle guide tube which is free of the C-shaped sleeve, simple in construction, simple and convenient in manipulation, has a needles firmly secured inside the guide tube during storage, remains secured in the tube without additional manipulations after removal from the package, and is pressed against the inner wall of the tube and parallel to the longitudinal axis of the guide tube. The invention also provides a method of securing an acupuncture needle inside the guide tube for reliable fixation of the needle inside the guide tube during storage and after unpacking prior to use.

Although the invention has been described with reference to specific embodiments, it is understood that the invention is not limited by these embodiments and that any changes and modifications are possible, provided they do not depart from the scope of the attached patent claims. For example, the transverse slot may have a triangular, rectangular, circular, or any other transverse configuration. The stopper can be made from materials other than those mentioned in the specification. The outer end of the stopper may have the same width as the end inserted into the slot. The guide tube can be made of glass, plastic, or any other transparent or non-transparent material. The guide tube may have a close cross section different from circular, e.g., an oval, ellipsoidal, or the like. The needle may have no handle, or the handle portion can be made in the form of a thickened tail portion of the needle.

What I claim is:

1. An acupuncture device comprising: a guide tube of a closed cross section having a side wall, a longitudinal axis, an open proximal end, an open distal end, and a slot cut through said side wall in a direction substantially perpendicular to said longitudinal axis, said slot having a width; an acupuncture needle member with a needle tip on one end, said needle member being inserted into said guide tube so that said needle tip is located near said open distal end of said guide tube but does not project therefrom; and a stopper member which possesses elasticity and which is inserted into said guide tube through said slot to provide friction contact between said needle member and said side wall sufficient to secure said needle member inside said guided tube, the end of said needle member opposite to said needle tip protrudes from said open proximal end of said guide tube.

2. The acupuncture device of claim 1, wherein said slot has a V-shape configuration in a side view perpendicular to the direction of insertion of said stopper member.

3. The acupuncture device of claim 2, wherein said slot has a depth not exceeding half-diameter of said guide tube.

4. The acupuncture device of claim 2, wherein said V-shape configuration is formed by a fist cut plane, which is substantially perpendicular to said direction of insertion of said stopper member, and a second cut plane, which is inclined to said first cut plane at an acute angle.

5. The acupuncture device of claim 1, wherein said slot has a depth not exceeding half-diameter of said guide tube.

6. The acupuncture device of claim 1, wherein said stopper member comprises a strip made of a material selected from the group consisting of plastic, rubber, wood, and thick paper.

7. The acupuncture device of claim 6, wherein said stopper member has an outer end which remains outside of said guide tube when said stopper is inserted into said guide tube through said slot.

8. The acupuncture device of claim 7, wherein said outer end has at least on its part a width greater than said width of said slot.

9. The acupuncture device of claim 7, wherein said outer end is bent and forms an angle with said wall of said guide tube.

10. The acupuncture device of claim 1, wherein said end of said needle member opposite to said needle tip has a needle handle.

11. The acupuncture device of claim 10, wherein said slot has a V-shape configuration in a side view perpendicular to the direction of insertion of said stopper member.

12. The acupuncture device of claim 10, wherein said slot has a depth not exceeding half-diameter of said guide tube.

13. The acupuncture device of claim 11, wherein said slot has a depth not exceeding half-diameter of said guide tube.

14. The acupuncture device of claim 11, wherein said V-shape configuration is formed by a fist cut plane, which is substantially perpendicular to said direction of insertion of said stopper member, and a second cut plane, which is inclined to said first cut plane at an acute angle.

15. The acupuncture device of claim 10, wherein said stopper member comprises a strip made of a material selected from the group consisting of plastic, rubber, wood, and thick paper.

16. The acupuncture device of claim 15, wherein said stopper member has an outer end which remains outside of said guide tube when said stopper is inserted into said guide tube through said slot.

17. The acupuncture device of claim 16, wherein said outer end has at least on its part a width greater than said width of said slot and is provided with friction means for improving conditions for gripping and removal of said stopper from said guide tube.

18. The acupuncture device of claim 17, wherein said outer end has friction means for improving conditions of gripping said outer end for removal thereof from said guide tube.

19. The acupuncture device of claim 16, wherein said outer end is bent and forms an angle with said wall of said guide tube.

20. A method of securing an acupuncture needle in an acupuncture device comprising a guide tube and an acupuncture needle inserted into said guide tube, said guide tube having a longitudinal axis and a side wall, said method comprising the steps of:

- cutting a slot in said side wall in a direction substantially perpendicular to said longitudinal axis;
- inserting said acupuncture needle into said guide tube to a required position;
- providing a stopper suitable for inserting into said slot from outside of said guide tube to said acupuncture needle; and
- securing said acupuncture needle in said guide sleeve by inserting said stopper into said slot to a position of contact with said acupuncture needle with a friction force sufficient for pressing said acupuncture needle to said side wall and for securing said needle inside said guide tube.

21.The method of claim 20, wherein said slot has a V-shape configuration in a side view perpendicular to the direction of insertion of said stopper member.

22. The method of claim 21, wherein said slot has a depth not exceeding half-diameter of said guide tube.

23. The method of claim 21, wherein said V-shape configuration is formed by a fist cut plane, which is substantially perpendicular to said direction of insertion of said stopper member, and a second cut plane, which is inclined to said first cut plane at an acute angle.

24. The method of claim 20, wherein said slot has a depth not exceeding half-diameter of said guide tube.

25. The method of claim 20, wherein said stopper member comprises a strip made of a material selected from the group consisting of plastic, rubber, wood, and thick paper, said stopper member having an inner end insertable into said guide tube through said slot, said inner end having a width, and an outer end which remains outside of said guide tube when said stopper is inserted into said guide tube through said slot, said outer end having, at least on a part of its length, a width wider than said width of said inner end.

* * * * *